United States Patent
Bacher

(10) Patent No.: US 6,508,809 B1
(45) Date of Patent: Jan. 21, 2003

(54) DEVICE FOR CONNECTING A PLURALITY OF APPARATUS AND INSTRUMENTS OF A MEDICO-TECHNICAL SYSTEM

(75) Inventor: Frank Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/559,493

(22) Filed: Apr. 27, 2000

(30) Foreign Application Priority Data

Oct. 29, 1999 (DE) .......................... 199 52 278

(51) Int. Cl.[7] .............................................. A61B 17/00
(52) U.S. Cl. .......................................... 606/1; 439/488
(58) Field of Search .......................... 606/1; 248/68.1; 604/19; 433/91, 92, 96, 80; 600/132, 156; 439/488, 489, 491

(56) References Cited

U.S. PATENT DOCUMENTS

| 4,619,640 A | * | 10/1986 | Potolsky et al. ............. 128/912 |
| 4,988,062 A | * | 1/1991 | London ................ 128/DIG. 26 |
| 5,224,674 A | * | 7/1993 | Simons ....................... 248/68.1 |
| 5,342,356 A | * | 8/1994 | Ellman et al. ................. 606/32 |
| 5,421,340 A | * | 6/1995 | Stanga et al. .......... 128/204.23 |
| 5,423,750 A | * | 6/1995 | Spiller .......................... 604/173 |
| 5,498,158 A | * | 3/1996 | Wong ........................... 433/102 |
| 5,790,896 A | * | 8/1998 | Nguyen ....................... 439/169 |
| 6,080,120 A | * | 6/2000 | Sandman et al. ............ 601/152 |
| 6,168,458 B1 | * | 1/2001 | Kraft ............................. 439/189 |

* cited by examiner

Primary Examiner—Linda C. M. Dvorak
Assistant Examiner—Kenneth Schopfer
(74) Attorney, Agent, or Firm—St. Once Steward Johnston & Reens LLC

(57) ABSTRACT

The invention concerns a device for connecting a plurality of apparatuses and instruments of a medico-technical system with various functions and circuits, a system encompassing several areas and diverse types of components, using connection and linking cables and tubes, and in which various colors are coordinated with individual sectors of the system while geometric symbols correspond to certain types of system components and markers are used for certain connectors. Thus, the connectors of apparatuses and instruments are designated with the color of the respective area, with the geometric symbol of the respective type of component, and with the assigned marker. The links in the connection and linking cables and tubes are designated with the color, symbol, and marker of the assigned area, component type, and marking. As a result, the related apparatus and instrument connectors and cable and tube connectors are identified by the combination of color, symbol, and marker.

4 Claims, 5 Drawing Sheets

Figure 1:
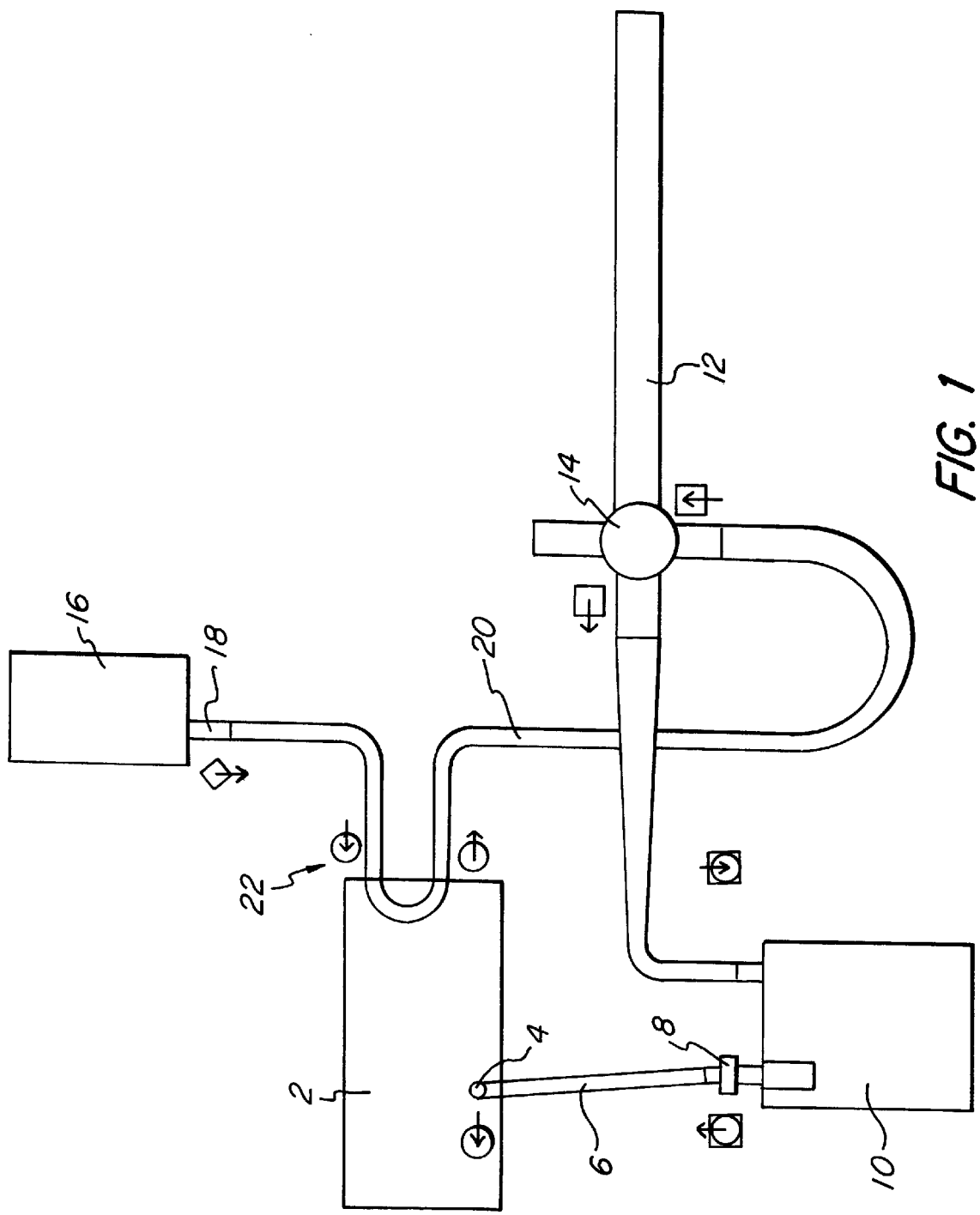

DEVICE FOR CONNECTING A PLURALITY OF APPARATUS AND INSTRUMENTS OF A MEDICO-TECHNICAL SYSTEM

FIELD OF THE INVENTION

The invention concerns a device for connecting a plurality of apparatuses and instruments of a medical-technical system.

BACKGROUND OF THE INVENTION

Work areas for endoscopic operations are equipped with a number of apparatuses that are connected by various tubes and cables. This results in the use of the most diverse configurations of apparatuses, tubes, and cables. Consequently considerable time is required for constructing the individual operating systems. In addition, the multiple tube and cable lines can pose a safety hazard. Where the user is concerned, preparations for an operation often lead to glitches that can cause delays of the operation itself. Problems in connecting individual units are further increased when time pressure is a factor, such as in cases where an additional apparatus is required during an operation.

One major problem that occurs is that cables and tubes lead partly through sterile areas and partly through non-sterile areas. Then, if the wrong end of a tube or cable is removed from the sterile area, it will have to be re-sterilized before it is reintroduced into the sterile area, causing considerable delay, or a new tube or cable must be used, which will require the availability of a sufficient supply.

It can also occur that the various units of such a medico-technical system are not correctly connected to one another. Although several connecting joints and the like are available, they are of limited variety. If the connectors are exchanged or even if someone simply uses the wrong connectors, the consequences for the patient can be serious.

Proposed solutions for ergonomic improvements in endoscopic apparatuses and systems in the operating area are for the most part based on improved arrangement of apparatuses and better design of service appliances. For instance, apparatuses are combined into apparatuses and video monitors are used. Practical results have been minimal, in terms of the hazards and the demands for connection and linking hook-ups for individual units such as rinsing pumps, insufflators, high voltage generators, suction pumps, light sources, camera systems, and the like.

SUMMARY OF THE INVENTION

The invention is based on the task of making it possible to construct and expand a medico-technical apparatus and instrument system quickly and without mishap.

This invention solves the task by means of a device with the characteristics listed in claim 1. Useful elaborations of the device of this invention are presented in the subsidiary claims.

The subject of the invention, then, is a device for connecting a plurality of apparatuses and instruments of a medico-technical system with various functions and circuits, a system encompassing several areas and diverse types of components, using connection and linking cables and tubes, and in which various colors are coordinated with individual sectors of the system while geometric symbols correspond to certain types of system components and markers are used for certain connectors. Thus, the connectors of apparatuses and instruments are designated with the color of the respective area, with the geometric symbol of the respective type of component, and with the assigned marker. The links in the connection and linking cables and tubes are designated with the color, symbol, and marker of the assigned area, component type, and marking. As a result, the related apparatus and instrument connections and cable and tube connections are identified by the combination of color, symbol, and marker.

The invention's device has the effect of a key system; that is, by optical means the individual parts of the apparatus and instrument system are combined with one another, just as a plug with a prong is connected thereby to an outlet equipped with a corresponding socket. Thanks to the existence of the color, symbol, and marker designation, it is no longer necessary in setting up a system to know its function and components precisely down to the last unit. Instead, different areas of a medico-technical system are set off from one another and individual types of components are effectively and immediately individualized. This also enables persons less familiar with the device's individual components to carry out the installation of a medico-technical system with reasonable speed and without error.

One important aspect of the invention's system is that the various apparatuses and instruments, including their connecting and supplementary components, can be set up in their connecting areas in a unified and clear manner. The connections can be immediately understood visually and without knowledge of a symbolic meaning of the various colors or signs, and the system units are easy to manipulate.

It is advisable to provide intermediate containers or apparatuses with a geometric symbol linking them to the instruments or apparatuses of the respective branch of the system. In this way the components of the individual branches can be assembled more quickly. Basic components therefore should be marked with a symbol that shows their position in the branch of the system; that is, the position is clearly indicated by the geometric symbol.

The tasks of connecting the parts is made especially clear and simple if markers designate the input and output points of apparatuses and instruments, so that the flow directions and adjoining areas are indicated.

Through the invention's visual design of the various apparatuses, instruments, and their connections, the connection to be established among the various units of a system made up of these apparatuses and instruments can be presented with simple means.

This is particularly important because of the predominance of purchased units, which vary quite widely in design and include diverse sorts of connections.

BRIEF DESCRIPTION OF THE INVENTION

Figure 2:
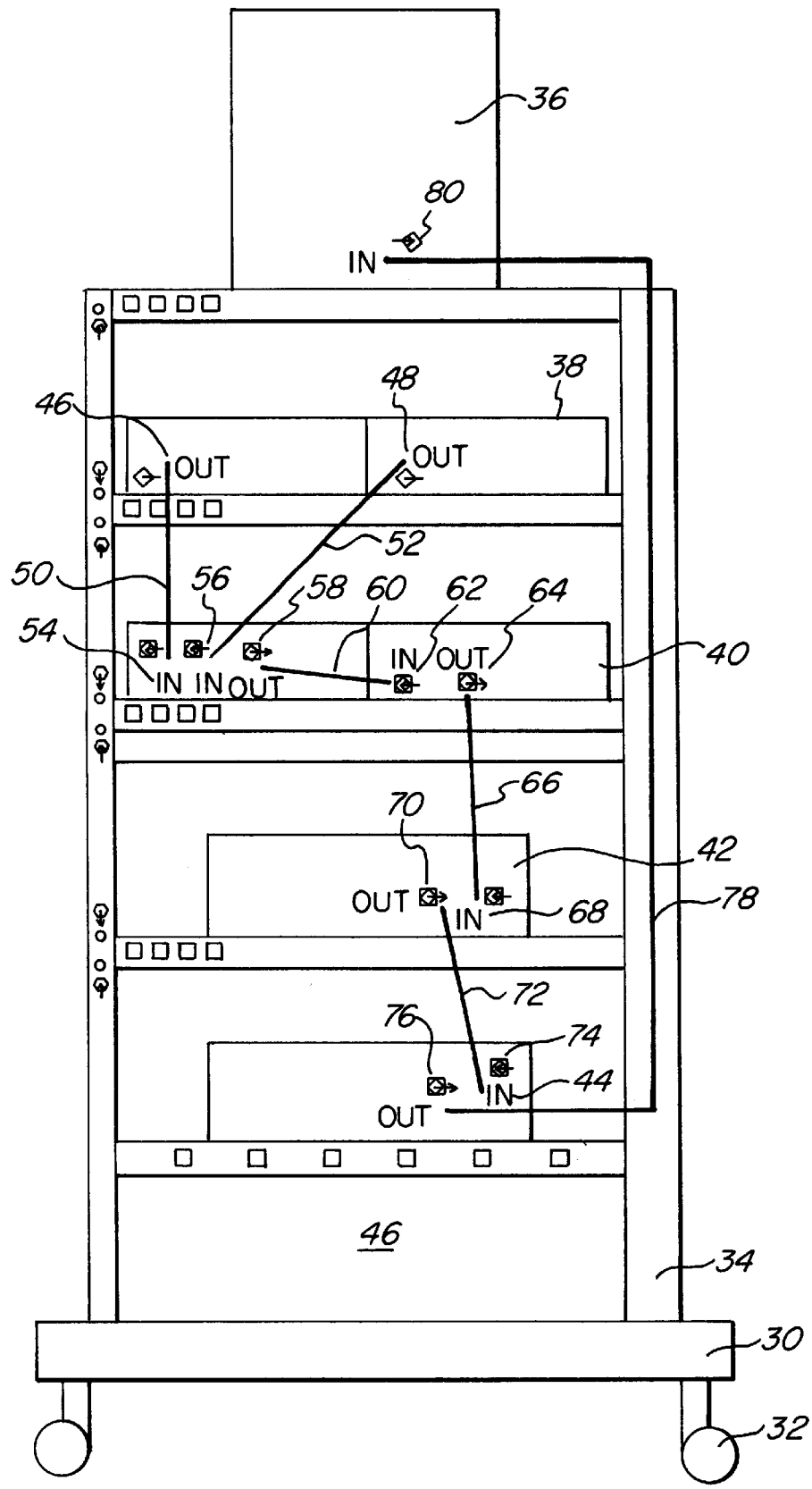
Figure 3:
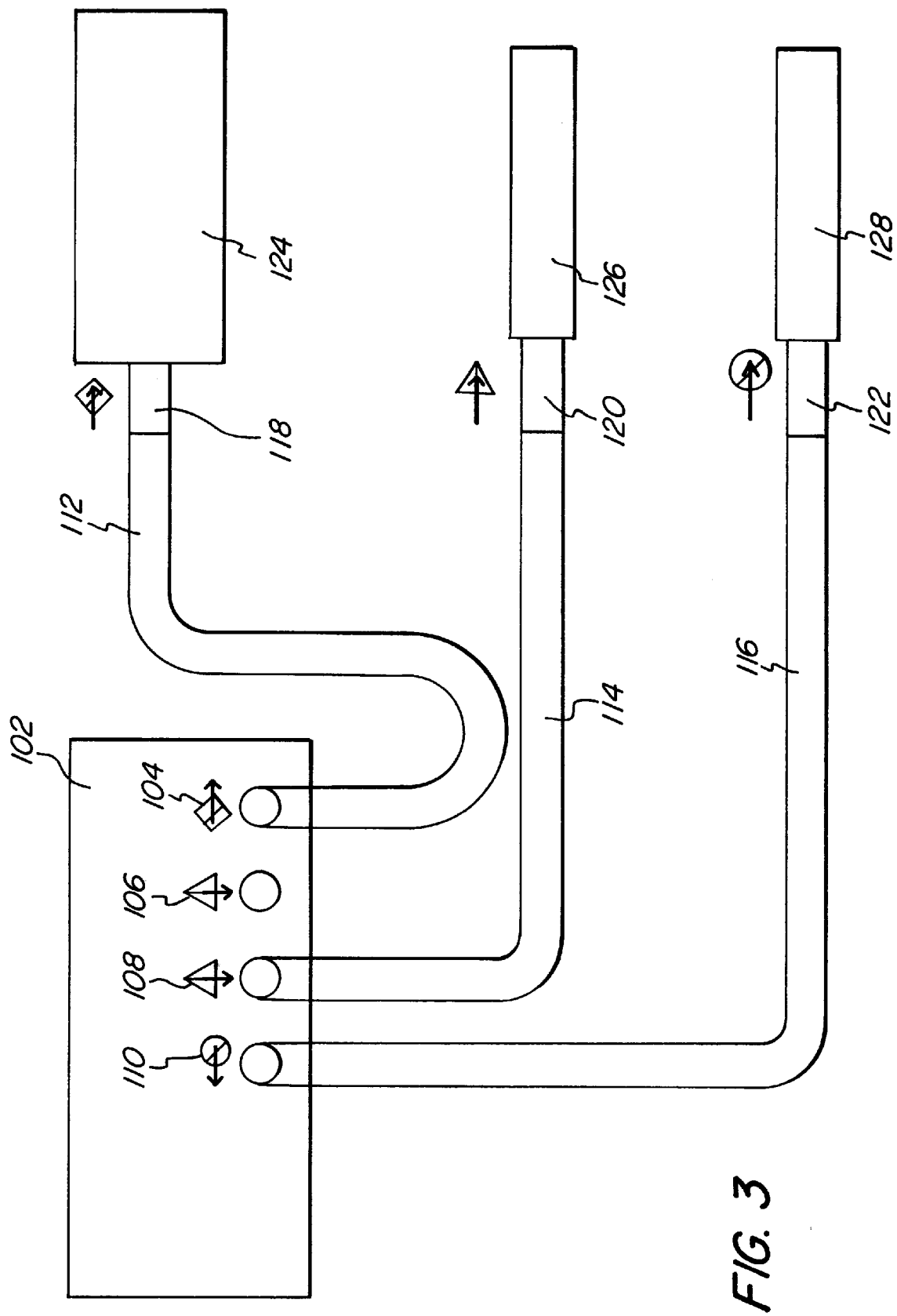
Figure 4A:
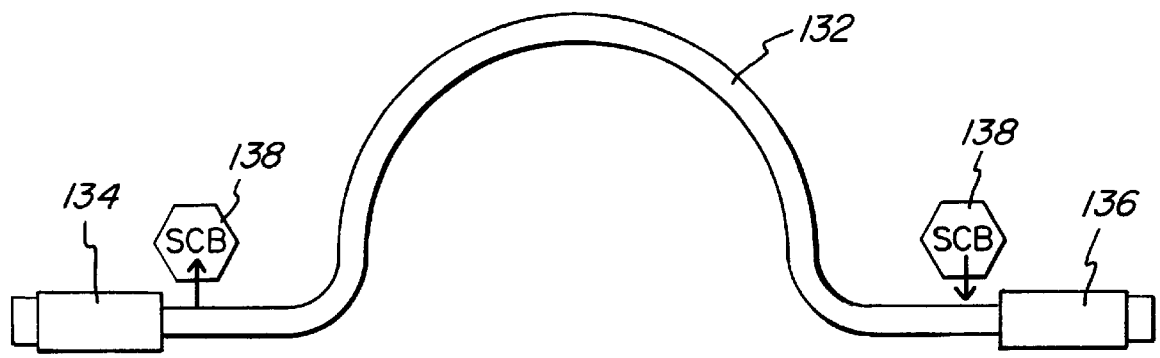
Figure 4B:
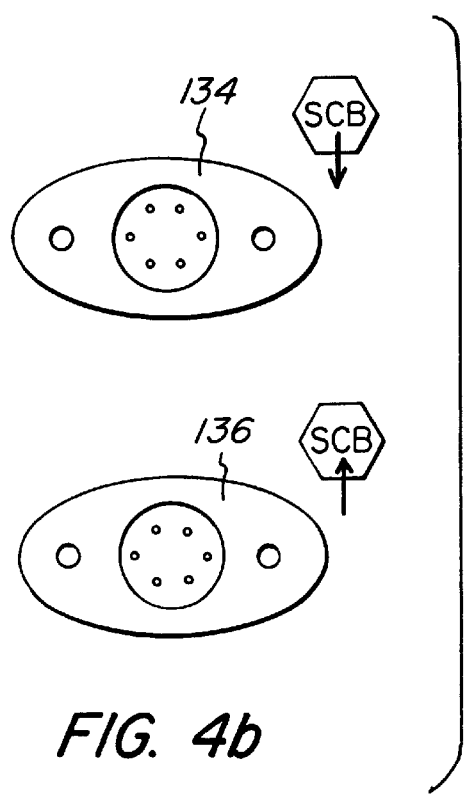

The invention is elucidated in further detail below by means of examples and sketches. The illustration is explanatory in nature and the invention is not to be restricted to the combinations of characteristics illustrated here. The illustrations are as follows:

FIG. 1 Schematic depiction of a suction and rinsing system for a medicotechnical system in the operating area FIG. 2 Schematic depiction of the cables linking a video system for a medico-technical system in the operating area FIG. 3 Example of the connection of an endoscopic instrument FIG. 4 Example of an SCB cable, that is, a cable for a commercially available modular communication system of the company Karl Storz GmbH & Co. KG for endoscopic operating systems, seen in lateral views (a) and in two frontal views (b)

Figure 5:
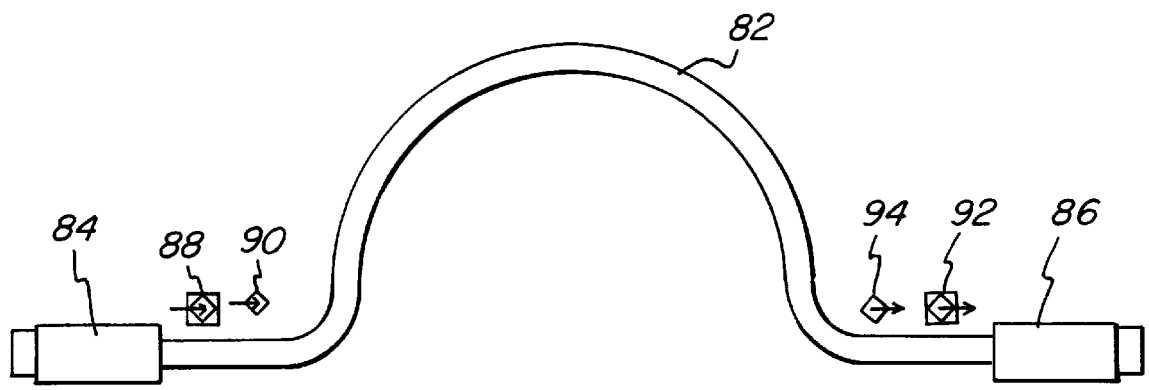

FIG. 5 Example of a video cable

Figure 6:
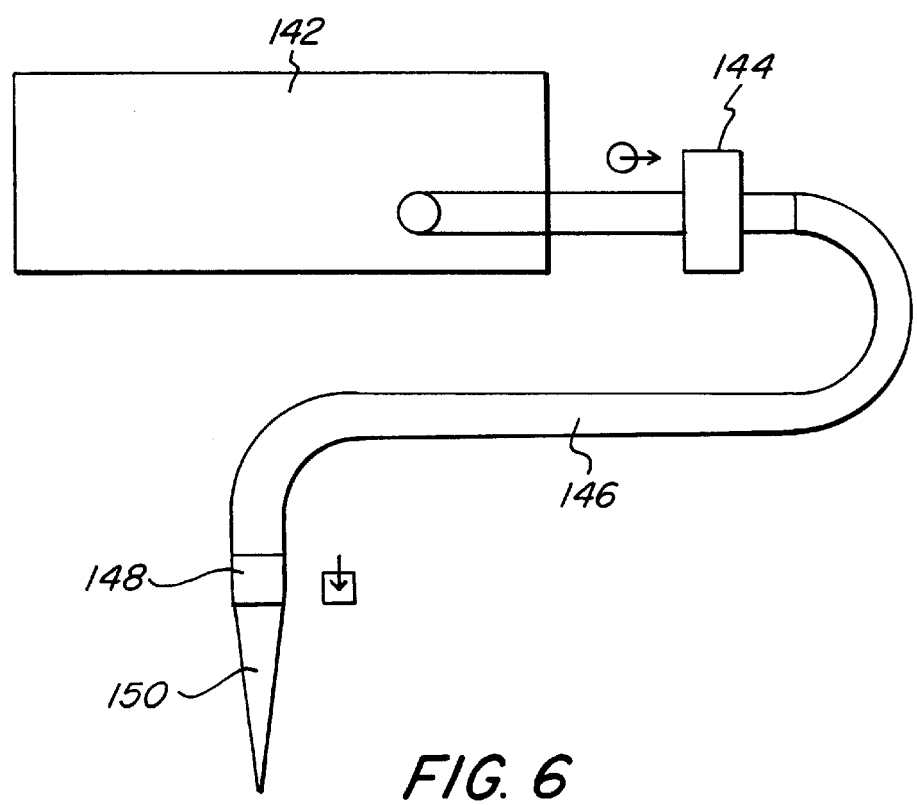

FIG. 6 Schematic depiction of the connection in the field of insufflation

DETAILED DESCRIPTION OF THE DRAWINGS

We refer first to FIG. 1, which shows a suction and rinsing system for a medico-technical system in the operating area. The main apparatus of this rinsing system is an endomat 2, which is used primarily in laparoscopy and gynecology to control rinsing fluid. Through the endomat, pressure, flow-through, and suction values can be entered and controlled during the operation, with the further assistance of a rotary pump 22, which is further mentioned hereafter A container 16 for rinsing fluid is connected at its outlet 18 with a connected line 20 to the endomat 2, which as mentioned above controls the operation of a rotary pump 22, by which the rinsing fluid is pumped out of the container 16. The tubing 20 leads to a multi-channel faucet, which in the drawing in FIG. 1 is set to the rinsing function.

The portion seen so far is the rinsing area, which is coded with the color red. The portions for the suction and rinsing system, described below, come under the suction area, which is coded with the color white. If the relevant system components are apparatuses (see the endomat 2, aspirator 10, rotary pump 22), they are marked with a circular symbol. In the case of the aspirator 10, which is built into the system as an intermediary apparatus, a square surrounds the circle.

The outlet connectors have an arrow pointing outward from the respective symbol, and the inlet connectors have an arrow pointing in toward the symbol.

Leading from the multi-channel faucet 14 is a line 12, which leads into the aspirator 10. Not shown in the sketch are the connectors and lines for additional rinsing operations, for which the rinsing fluid of the container 16 may also be used. An outlet connector 8 from the aspirator 10 is connected with an outlet tube 6, which is linked to an inlet connector 4 of the endomat 2.

FIG. 2 illustrates the cabling of a video system, which is installed on a cart 30 that can move on rollers 32. The cart 30 carries a framework 34 on which a video monitor 36 stands. Installed in the framework 34 are various components of the video system, of which the illustration shows a recorder 38 with a so-called telecam or tricam system (a camera system of Storz GmbH & Co. KG), a control mechanism 40, a printer 42, a recording device 44, and a selective transformer 46 (merely referred to in the sketch). The output connectors 46, 48 of the recorder 38 are linked by cables 50, 52 with input connectors 54, 56 of the control mechanism of the twin type and with the image processing part, and its output connector 58 is connected by way of cable 60 with the input connector 62 of the image processing part of the control mechanism 40, by means of which the image on the video monitor 36 can be modified as desired by the operator. The output connector 64 of the image processing part is connected by way of a cable 66 with the input connector 68 of the printer 42. A cable 72 leads from the output connector of the printer 42 to the input connector 74 of the recorder 44. A cable 78 connects the output connector 76 of the recorder 44 with the input connector 80 of the video monitor.

The connector sockets and prongs all bear green symbols or markings. The input and output connectors 46, 48, 80 have diamond-shaped symbols.

The remaining apparatuses are intermediary devices; that is, their connectors bear the symbol of a circle surrounded by a square. The cables are marked with the same signs as the apparatuses. Provided that the cable ends can be affixed at will, the signs accordingly are kept flexible, since a varying number of apparatuses can be used. However, the connection must always be made from an output to an input connector.

FIG. 5 shows an example of a video cable 82, which has a four-channel line with 4-Pol-Mini-DIN prongs 84, 86. The prong 84 seen at the viewer's left in FIG. 5 bears markings 88, 90 for attachment to an output connector of an intermediate or terminal apparatus. The other (right-hand) prong 86 bears markings 92, 94 for attachment to an input connector of an intermediate or terminal apparatus. The video cable 82 could thus be any of the cables depicted in FIG. 2 assuming the same length.

FIG. 3 shows an example of the connection of an endoscopic instrument, in this case a high voltage incision and coagulation apparatus (color coding blue/yellow). A control mechanism 102 has four connectors, namely a neutral electrode connector 104, two monopolar electrode connectors 106, 108, and a bipolar electrode connector 110, of which three connectors are used in the example shown in FIG. 3. Cables 112, 114, 116 lead to the input connectors 118, 120, 122 of a neutral electrode 124, a monopolar electrode 126, and a bipolar electrode 128. No doubt, because of their shape, the prongs cannot be inserted into the wrong electrode connectors. Nevertheless a marking, as foreseen by the invention as a visual key, is very useful. Thus for instance the connector 122 for an SCB cable, that is, a six-channel line with 6-Pol-Min-DIN prongs, is provided and therefore has received a hexagonal marker. This measure prevents the wrong end of the cable from being inserted, first, in the control mechanism 102, which can be located in the non-sterile area, and secondly the non-compatibility of the prong end with the apparatus connector is made clear. The marker 122 is thus nothing other than the visualization of the cable connection or of its type, and thus makes it unnecessary for the installation staff to make a thorough examination of the connection. FIG. 3 does not show the operating elements of the control mechanism 102.

FIG. 4 shows an example of an SCB cable 132 with connector prongs 134, 136. As the front view (b) of both prongs 134, 136 shows, they are interchangeable. This is made clear by the commonly used gray connector markers 138.

An example of a connection from the insufflation field, denoted by the color brown, is seen in FIG. 6. A tube 146 is connected to the outlet connector 144 of an electronic insufflator 142, and an insufflation needle 150 is connected with this tube's outlet connector 148.

What is claimed is:

1. A device for connecting a plurality of apparatuses and instruments of a medical system, comprising:

a plurality of instrument connectors;

a plurality of receiver connectors;

said plurality of instrument connectors and said plurality of receiver connectors defining a first plurality of subsets, each of said first plurality of subsets having a color associated therewith, wherein the color associated with each subset is visually distinct from the colors associated with other subsets;

each of said first plurality of subsets comprising a second plurality of subsets, each of said second plurality of subsets having a symbol associated therewith;

each of said second plurality of subsets comprising a third plurality of subsets, each of said third plurality of subsets having a marker associated therewith; and wherein each of said plurality of instrument connectors and each of said plurality of receiver connectors includes the color, symbol, and marker corresponding to said first plurality of subsets, said second plurality of subsets, and said third plurality of subsets with which it is associated to facilitate matching of corresponding instrument connectors and receiver connectors.

2. The system according to claim 1, wherein the symbols for said second plurality of subsets of said plurality of receiver connectors and said plurality of instrument connectors are associated with basic and terminal components.

3. The system according to claim 1, wherein the symbols for said second plurality of subsets of said plurality of receiver connectors and said plurality of instrument connectors are associated with intermediary containers or apparatuses.

4. The system according to claim 1, wherein the markers for said third plurality of subsets of said plurality of receivers and said third plurality of subsets of said plurality of instrument connectors are associated with input and output.

* * * * *